US009521990B2

United States Patent
Zelenka et al.

(10) Patent No.: US 9,521,990 B2
(45) Date of Patent: Dec. 20, 2016

(54) VARIABLE-STIFFNESS IMAGING WINDOW AND PRODUCTION METHOD THEREOF

(75) Inventors: Robert Zelenka, Milpitas, CA (US); Ruth E. Beeby, Mountain View, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 318 days.

(21) Appl. No.: 13/468,705

(22) Filed: May 10, 2012

(65) Prior Publication Data

US 2012/0289837 A1 Nov. 15, 2012

Related U.S. Application Data

(60) Provisional application No. 61/484,941, filed on May 11, 2011.

(51) Int. Cl.
| | |
|---|---|
| *A61B 8/00* | (2006.01) |
| *A61B 8/12* | (2006.01) |
| *B29C 65/18* | (2006.01) |
| *B29C 65/68* | (2006.01) |
| *B29C 65/00* | (2006.01) |
| *B29L 31/00* | (2006.01) |

(Continued)

(52) U.S. Cl.
CPC .............. *A61B 8/445* (2013.01); *A61B 8/12* (2013.01); *B29C 61/006* (2013.01); *B29C 65/02* (2013.01); *B29C 65/18* (2013.01); *B29C 65/68* (2013.01); *B29C 66/0042* (2013.01); *B29C 66/1142* (2013.01); *B29C 66/1282* (2013.01); *B29C 66/12841* (2013.01); *B29C 66/5221* (2013.01); *B29C 66/63* (2013.01); *B29C 66/71* (2013.01); *B29C 66/8122* (2013.01); *B29C 66/919* (2013.01); *B29C 66/91421* (2013.01); *B29L 2031/7542* (2013.01)

(58) Field of Classification Search
USPC ................................ 600/437, 459, 462, 466
See application file for complete search history.

(56) References Cited

U.S. PATENT DOCUMENTS

| | | | |
|---|---|---|---|
| 4,636,346 | A | 1/1987 | Gold et al. |
| 4,870,887 | A | 10/1989 | Tresslar |
| 5,037,404 | A | 8/1991 | Gold |

(Continued)

FOREIGN PATENT DOCUMENTS

| | | |
|---|---|---|
| CN | 1810213 A | 8/2006 |
| EP | 1955724 A1 | 8/2008 |

(Continued)

OTHER PUBLICATIONS

PCT/US2012/037627, International Search Report and Written Opinion dated Feb. 26, 2013, 10 pages.

(Continued)

*Primary Examiner* — Rochelle Turchen
(74) *Attorney, Agent, or Firm* — Fredrikson & Byron, P.A.

(57) ABSTRACT

An imaging window of an imaging catheter includes a first imaging window section and a second imaging window section. The first imaging window section has a finite length and is formed from a first material having a flexural modulus. The second imaging window section has a finite length and is formed from a second material having a flexural modulus. The flexural modulus of the first material is different than the flexural modulus of the second material.

8 Claims, 7 Drawing Sheets

(51) Int. Cl.
 B29C 61/00 (2006.01)
 B29C 65/02 (2006.01)

(56) References Cited

U.S. PATENT DOCUMENTS

| | | | |
|---|---|---|---|
| 5,201,316 A | 4/1993 | Pomeranz et al. |
| 5,240,985 A | 8/1993 | Gardiner |
| 5,250,069 A | 10/1993 | Nobuyoshi |
| 5,312,356 A | 5/1994 | Engelson |
| 5,316,706 A | 5/1994 | Muni et al. |
| 5,330,444 A | 7/1994 | Webler et al. |
| 5,399,164 A | 3/1995 | Snoke |
| 5,400,785 A | 3/1995 | Crowley |
| 5,443,457 A | 8/1995 | Ginn et al. |
| 5,531,721 A | 7/1996 | Pepin |
| 5,542,924 A | 8/1996 | Snoke |
| 5,624,397 A | 4/1997 | Snoke |
| 5,715,825 A | 2/1998 | Crowley |
| 5,720,300 A | 2/1998 | Fagan |
| 5,762,066 A | 6/1998 | Law et al. |
| 5,824,030 A * | 10/1998 | Yang et al. | 607/122 |
| 5,851,203 A | 12/1998 | van Muiden |
| 5,957,910 A | 9/1999 | Holden |
| 6,007,478 A | 12/1999 | Siess et al. |
| 6,264,633 B1 | 7/2001 | Knorig |
| 6,524,303 B1 | 2/2003 | Garibaldi |
| 6,610,068 B1 | 8/2003 | Yang |
| 6,712,766 B2 | 3/2004 | Harada |
| 6,929,635 B2 | 8/2005 | Shelso |
| 7,387,826 B2 | 6/2008 | Burgmeier et al. |
| 7,632,236 B2 | 12/2009 | Kaneto |
| 2002/0188189 A1 | 12/2002 | Belef |
| 2005/0090852 A1 | 4/2005 | Layne et al. |
| 2005/0101859 A1 | 5/2005 | Maschke |
| 2005/0125002 A1 | 6/2005 | Baran et al. |
| 2005/0142314 A1 | 6/2005 | Burgmeier et al. |
| 2005/0203396 A1 | 9/2005 | Angelsen et al. |
| 2005/0261586 A1 | 11/2005 | Makin et al. |
| 2006/0084964 A1 | 4/2006 | Knudson et al. |
| 2007/0167824 A1 | 7/2007 | Lee et al. |
| 2007/0240817 A1 | 10/2007 | Strong et al. |
| 2009/0163818 A1 | 6/2009 | Zelenka et al. |
| 2009/0270737 A1 | 10/2009 | Thornton |
| 2010/0185172 A1* | 7/2010 | Fabro | 604/500 |
| 2010/0204605 A1* | 8/2010 | Blakley et al. | 600/549 |
| 2012/0289837 A1 | 11/2012 | Zelenka et al. |
| 2013/0253328 A1 | 9/2013 | Zelenka et al. |

FOREIGN PATENT DOCUMENTS

| | | |
|---|---|---|
| JP | H05-084247 A | 4/1993 |
| JP | H08-140976 A | 6/1996 |
| JP | H08-275947 A | 10/1996 |
| JP | 2000152940 A | 6/2000 |
| JP | 2002109217 A | 4/2002 |
| JP | 2002528188 A | 9/2002 |
| JP | 2003210462 A | 7/2003 |
| JP | 3571939 B2 | 9/2004 |
| JP | 2005013453 A | 1/2005 |
| JP | 2005052667 A | 3/2005 |
| JP | 2006075611 A | 3/2006 |
| JP | 2007152101 A | 6/2007 |
| WO | 9221965 A1 | 12/1992 |
| WO | WO 98/50098 | 11/1998 |
| WO | 0033742 A2 | 6/2000 |
| WO | 2009134171 A1 | 11/2009 |
| WO | 2011027821 A1 | 3/2011 |
| WO | 2013169269 A1 | 11/2013 |

OTHER PUBLICATIONS

Giants, "Crystallinity and Dielectric Properties of PEEK, Poly (ether ether ketone)," Abstract, IEEE Transactions on Dielectrics and Electrical Insulation, vol. 1, No. 6, 1994.

Kurtz et al., "PEEK Biomaterials in Trauma, Orthopedic, and Spinal Implants," Biomaterials, vol. 28, No. 32, 2007, pp. 4845-4869.

U.S. Appl. No. 61/484,941, entitled "Variable-Stiffness Imaging Window and Production Method Thereof," filed May 11, 2011, 19 pages.

European Patent Application No. 12876242.4, Extended European Search Report mailed Apr. 12, 2016, 5 pages.

* cited by examiner

VARIABLE-STIFFNESS IMAGING WINDOW AND PRODUCTION METHOD THEREOF

PRIORITY CLAIM

The present application claims the benefit of U.S. Provisional Patent Application Ser. No. 61/484,941, filed May 11, 2011, which application is incorporated herein by reference in its entirety.

BACKGROUND

The present invention generally relates to catheters. The present invention further relates to catheters having sheaths with variable stiffness. The present invention still further relates to intravascular imaging catheters.

Percutaneous coronary interventions in patients suffering from coronary artery disease often involve deployment of a stent in order to keep open a coronary artery that supplies oxygenated blood to a patient's heart. An intravascular ultrasound imaging catheter may be used to assess adequacy of stent deployment, including the extent of stent apposition and determination of the minimum luminal diameter within the stent.

Current intravascular ultrasound imaging catheters having a mechanically rotating imaging core include an imaging window having a single flexural modulus. An imaging window having a single flexural modulus avoids measurement inaccuracies due to image artifacts that may be introduced by use of an imaging window having a variable flexural modulus, such as braided sleeves or extrusions of varying wall thickness. The flexural modulus, or stiffness, of the imaging window affects catheter pushability and catheter trackability. Pushability describes how a force transmitted longitudinally at the catheter proximal end is transferred to longitudinal movement of the catheter distal end. Trackability describes how easily the catheter is able to reach its destination (e.g., a coronary artery segment). The use of an imaging window with a single flexural modulus presents a trade-off between catheter pushability and trackability. Current intravascular ultrasound imaging catheters exhibit limitations in navigating some coronary arteries.

Safe and effective delivery of an intravascular ultrasound imaging catheter to a coronary artery requires an imaging window having sufficient pushability to reach the coronary artery and adequate trackability to navigate the tortuous coronary arteries. It would be advantageous if the stiffness of the imaging window could be varied with length in order to optimize the balance between catheter pushability and trackability. It would be further advantageous if the imaging window provides uniform imaging performance along its entire length.

SUMMARY

In one embodiment, an imaging window of an imaging catheter includes a first imaging window section, the first imaging window section having a finite length and being formed from a first material having a flexural modulus and a second imaging window section. The second imaging window section has a finite length and is formed from a second material having a flexural modulus. The flexural modulus of the first material is different than the flexural modulus of the second material.

The catheter has a proximal end and a distal end. The first imaging window section is proximal to the second imaging window section and the flexural modulus of the first material is greater than the flexural modulus of the second material.

The first and second materials are substantially transparent to ultrasound energy. The first and second materials are polyethylene materials. The first and second materials each have imaging performance characteristics that are substantially equivalent.

In another embodiment, an imaging catheter has an imaging window including a plurality of serially aligned imaging window sections, each imaging window section having a finite length and being formed from a material having a flexural modulus. The flexural modulus of the material forming each imaging window section is different from the flexural modulus of the material forming each of the other imaging window sections.

In another embodiment, a method of making an imaging window for use in an imaging catheter includes the steps of providing a mandrel having a anti-stick coating thereon, successively loading a plurality of imaging window tubing sections onto the mandrel, wherein each of the tubing sections has a flexural modulus and a flexural modulus different from the flexural modulus of the other tubing sections, joining the tubing sections end-to-end together to form an imaging window section, and removing the imaging window section from the mandrel.

The successively loading step may be performed by loading the imaging window tubing sections onto the mandrel in a given order corresponding to progressive change in the flexural modulus of the imaging window sections. The given order corresponds to a progressive increase in the flexural modulus of the imaging window tubing sections. The imaging window tubing sections are formed from polyethylene material.

The joining step may include applying heat to the imaging window tubing sections. The joining step may further include covering the imaging window tubing sections with a heat shrink tubing prior to applying heat to the imaging window tubing sections. The joining step may further include using a vertical laminator.

The plurality of imaging window tubing sections may form a first plurality of imaging window tubing sections to form a first imaging window section, and the method may further include successively loading a second plurality of imaging window tubing sections onto the mandrel, wherein each of the tubing sections of the second plurality of imaging window tubing sections has a flexural modulus and a flexural modulus different from the flexural modulus of the other tubing sections of the second plurality of imaging window tubing sections, placing a spacer tubing between the first and second pluralities of imaging window tubing sections, joining the tubing sections end-to-end together of the first and second pluralities of imaging window tubing sections to form first and second imaging window sections, respectively, and removing the first and second imaging window sections from the mandrel.

BRIEF DESCRIPTION OF THE DRAWINGS

The invention, together with further features and advantages thereof, may best be understood by making reference to the following descriptions taken in conjunction with the accompanying drawings, in the several figures of which like reference numerals identify identical elements, and wherein.

DETAILED DESCRIPTION OF THE EMBODIMENTS

Figure 1:
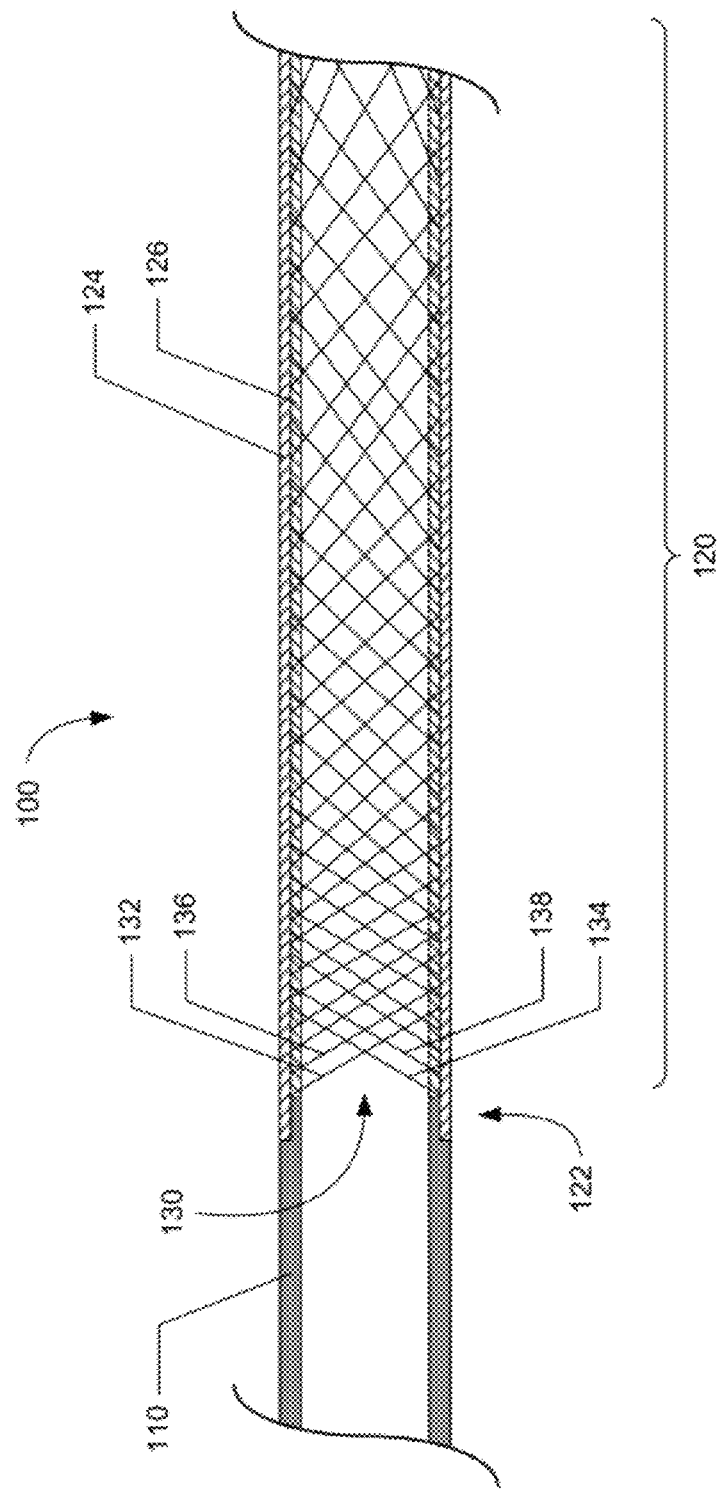
FIG. 1 is a partial sectional side view of a prior art catheter.

FIG. 1 shows a partial sectional side view of a prior art catheter 100 having a stiffness that varies with length. The catheter includes a proximal sheath 110 and a distal section 120. The distal section 120 includes a braided sleeve 130 wherein the braided sleeve has a continually reduced pitch and weave density in a direction from the proximal section 110 toward the catheter distal tip (not shown). The braided sleeve filaments 132,134,136,138 may be relatively hard materials, including metals or nylon. The braided sleeve provides increasing flexibility on progressing distally (i.e., to the right in FIG. 1). The progressive flexibility of the distal section 120 may be advantageous for catheter pushability and trackability, but the braided sleeve 130 is problematic for intravascular ultrasound imaging. The braided sleeve filaments 132,134,136,138 may cause undesirable scattering of the ultrasonic field and imaging artifacts.

Figure 2:
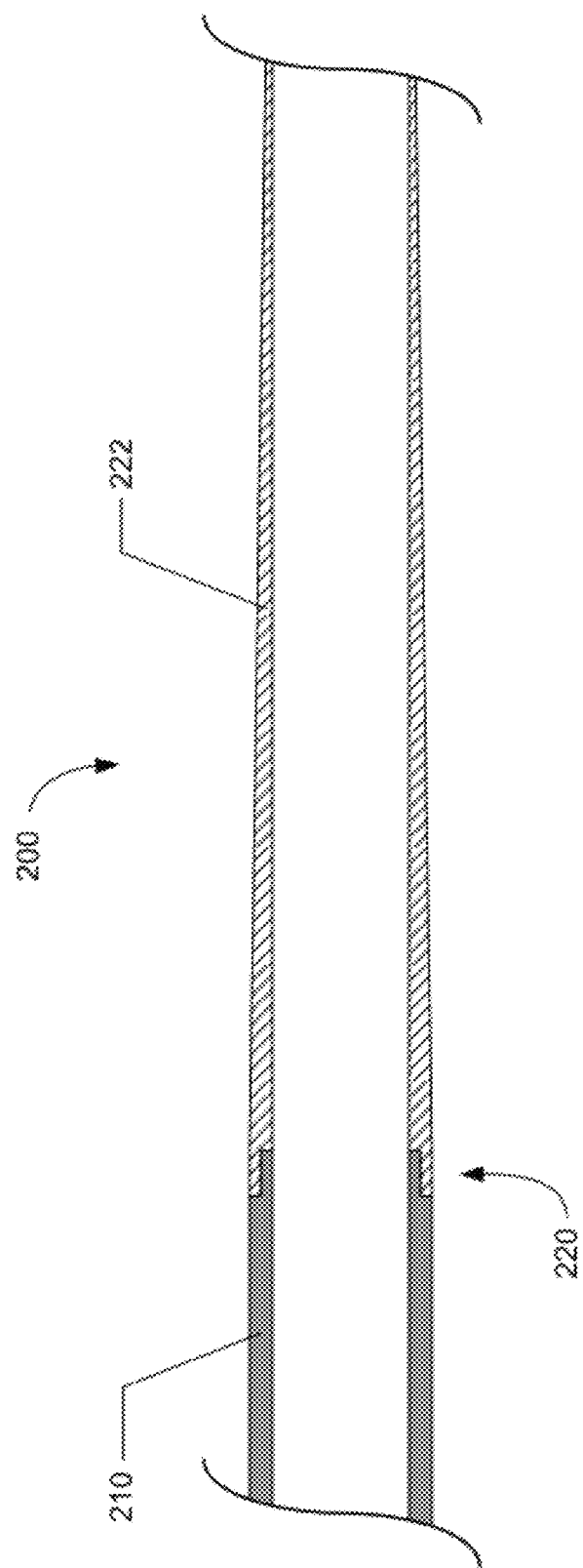
FIG. 2 is a partial sectional side view of another prior art catheter.

FIG. 2 shows a sectional side view of another prior art catheter 200 having a stiffness that varies with length. The catheter includes a proximal sheath 210 and a distal sheath 222. The wall thickness of the distal sheath 222 decreases with length and provides increasing flexibility on progressing distally (i.e., to the right in FIG. 2). The progressive flexibility of the distal sheath 222 may be advantageous for catheter pushability and trackability, but the varying wall thickness is problematic for intravascular ultrasound imaging. The varying wall thickness may lead to incorrect registration of vessel wall and stent position in ultrasound images and impact accuracy of lumen diameter and area measurements.

Figure 3:
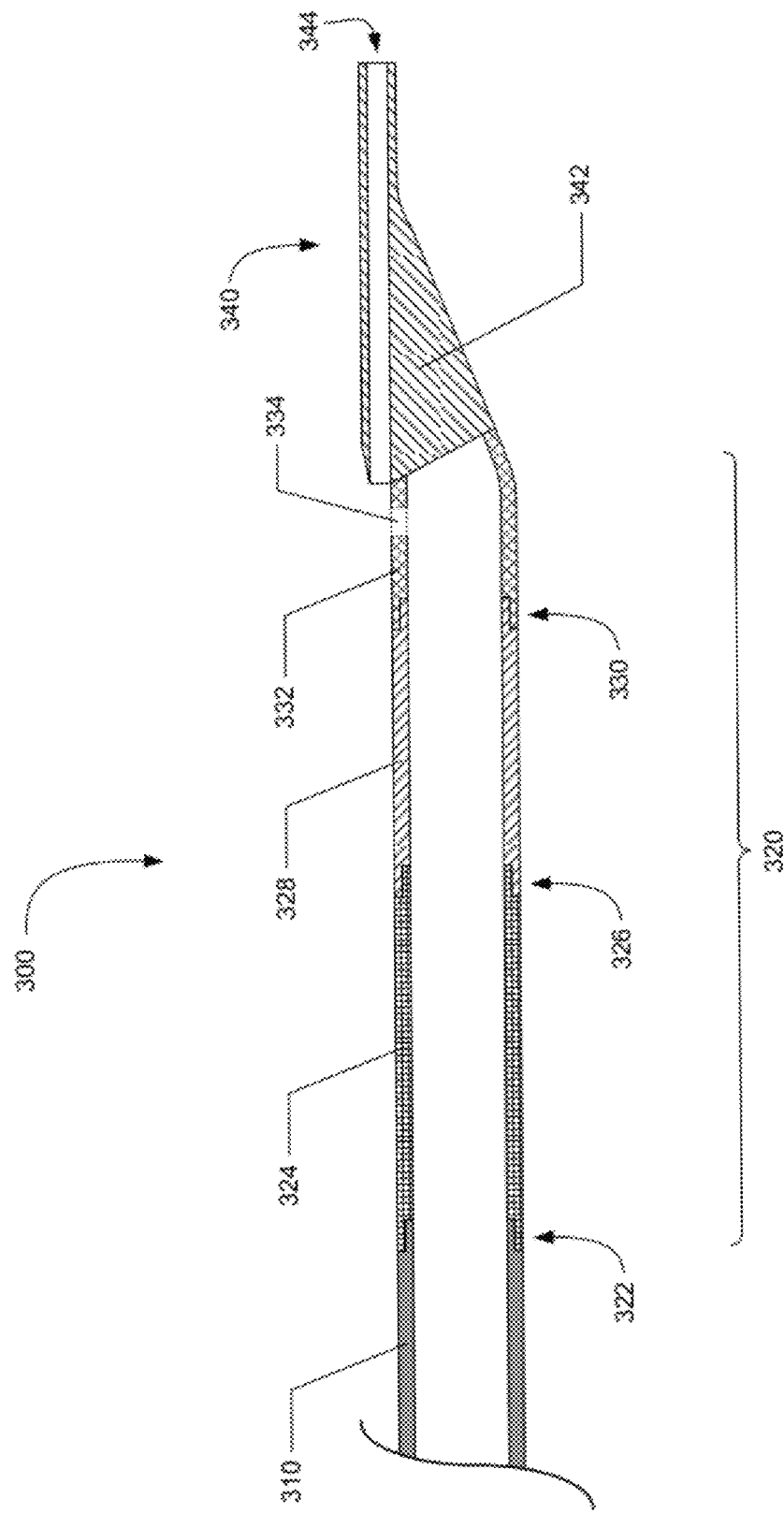
FIG. 3 is a partial sectional side view of a catheter embodying the invention.

Referring now to FIG. 3, a sectional side view of a monorail catheter 300 according to one embodiment of the present invention is shown. The catheter 300 includes a midshaft sheath 310, an imaging window 320, and a distal tip 340. The midshaft sheath 310 may be composed of high-density polyethylene (HDPE). The midshaft sheath 310 provides adequate pushability for the catheter and may have a flexural modulus in the range 200 kilopound per square inch (ksi) to 250 ksi, generally 225 ksi. The midshaft sheath 310 may be bonded to the imaging window 320 by means of thermal bonding, for example. The imaging window 320 may further be bonded to the distal tip 340. The distal tip 340 may take the form as described for example in additional detail in Published United States Patent Application, US2010/0057019, Published Mar. 4, 2010, the complete disclosure of which is hereby incorporated herein by reference. As an exemplary embodiment only and without limiting the invention, the following description will be directed to deployment in an intravascular ultrasound imaging catheter that is suitable for imaging of coronary arteries. Similarly, with no intention to limit the invention, the following description will be further directed at the case wherein the imaging window 320 includes three sections.

The outer diameter of the imaging window 320 may be constant and sufficiently small for the catheter to be delivered through a 6 F guide catheter. Further, the inner diameter of the imaging window 320 may be constant in the range 0.024" to 0.038", generally 0.0335". The imaging window wall thickness may be in the range 0.001" to 0.007", generally 0.005".

Polyethylene (PE) has been found to be a suitable material for an imaging window. Further, polyethylene is available in different flexural moduli, or stiffnesses. High-density polyethylene has a larger stiffness than low-density polyethylene (LDPE). Polyethylene sheaths of intermediate stiffness can be composed of medium density PE (MDPE) which can be formed from blends of HDPE and LDPE.

The three sections of the imaging window 320 include an imaging window proximal section 324, an imaging window middle section 328, and an imaging window distal section 332. The distal end of the imaging window proximal section 324 is bonded to the proximal end of the imaging window middle section 328. The distal end of the imaging window middle section 328 is bonded to the proximal end of the imaging window distal section 332. The length of the imaging window 320 may be in the range 100 mm to 200 mm, generally 100 mm to 150 mm. The length of the imaging window generally depends on the length of the vessel to be imaged. The stiffness of the imaging window 320 decreases proximally to distally. The imaging window proximal section 324 may be composed of HDPE and has a flexural modulus in the range 195 ksi to 245 ksi, generally 220 ksi. The length of the imaging window proximal section 324 may be in the range 40 mm to 100 mm, generally 70 mm. The imaging window middle section 328 is composed of MDPE and has a flexural modulus in the range 155 ksi to 205 ksi, generally 180 ksi. The length of the imaging window middle section 328 may be in the range 30 mm to 70 mm, generally 50 mm. The imaging window distal section 332 is composed of LDPE and has a flexural modulus in the range 35 ksi to 85 ksi, generally 60 ksi. The length of the imaging window distal section 332 may be in the range 10 mm to 50 mm, generally 20 mm.

Figure 4:
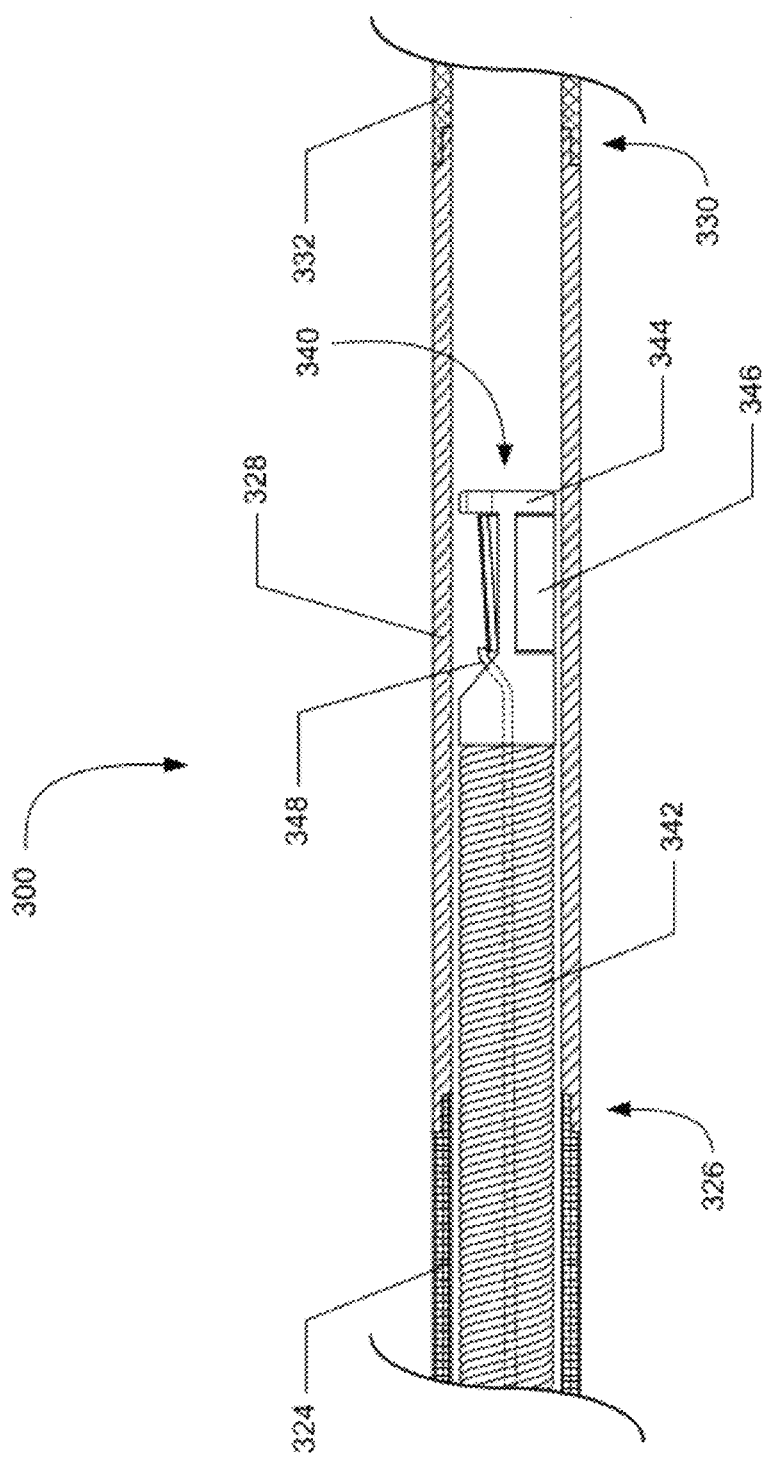
FIG. 4 is a partial sectional side view of a catheter embodying the invention.

Referring now to FIG. 4, the catheter 300 may more specifically include an imaging core 340 that further includes a flexible drive cable 342, a transducer housing 344, an ultrasonic transducer stack 346, and a transmission line 348. The variations in ultrasonic properties of the imaging window sections 324, 328, 332, including the speed of sound, acoustic impedance, and attenuation, are sufficiently low such that variation in imaging performance through the different imaging window sections is negligible. Further, the ultrasonic attenuation of the imaging window sections is sufficiently low such that the imaging window sections are substantially transparent to ultrasound energy.

One embodiment of a method for producing a variable-stiffness imaging window according to the present invention includes loading onto a polytetrafluoroethylene (PTFE) coated mandrel in sequence imaging window proximal tubing, imaging window middle tubing, and imaging window distal tubing. The imaging window tubing sections may be bonded by means of a vertical laminator heater. The production method of the imaging window of the present invention is not particularly limited. The following method represents one embodiment of the production method.

Figure 5:
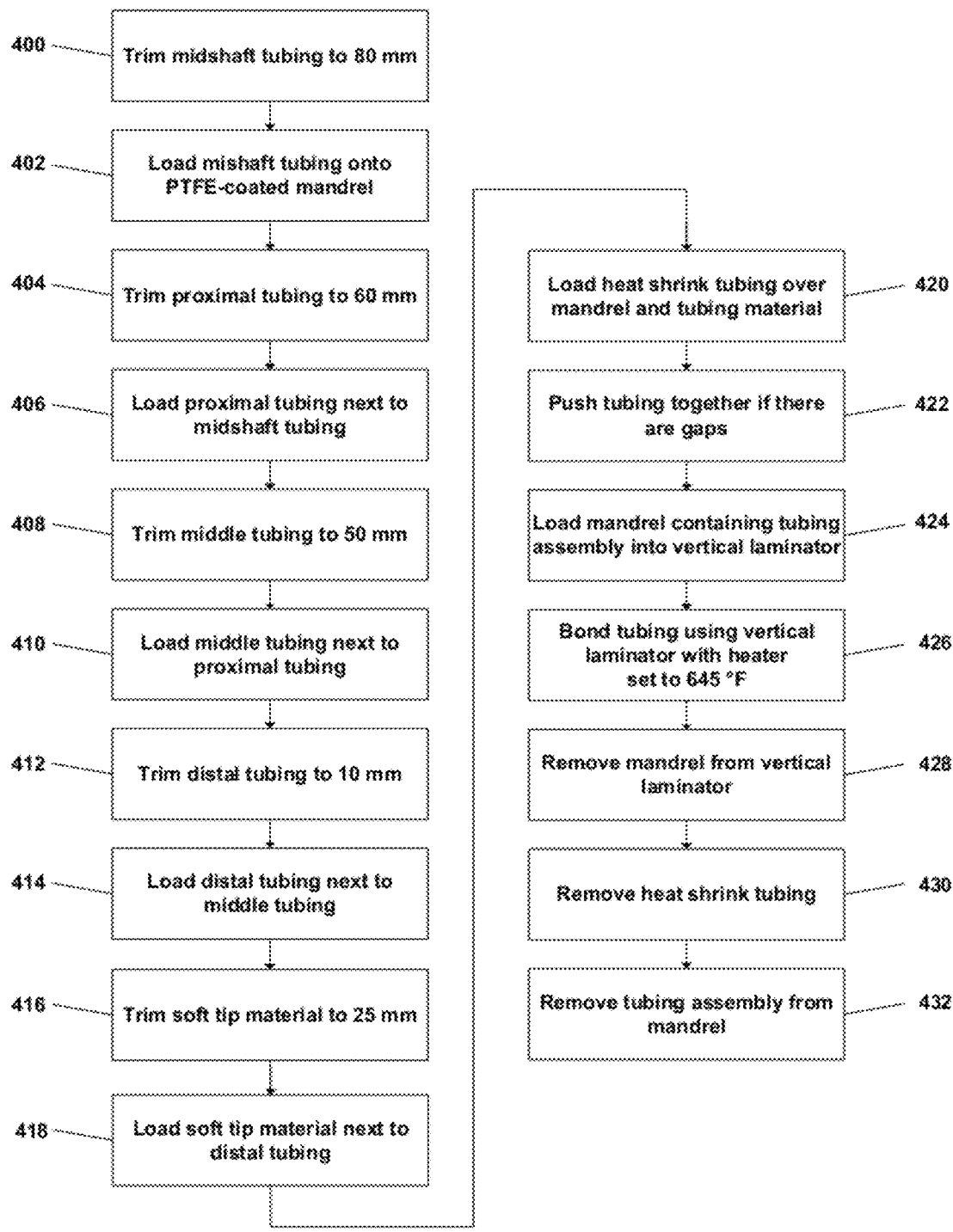
FIG. 5 is a flow diagram illustrating processing steps for manufacturing an imaging window embodying the invention.
Figure 6:
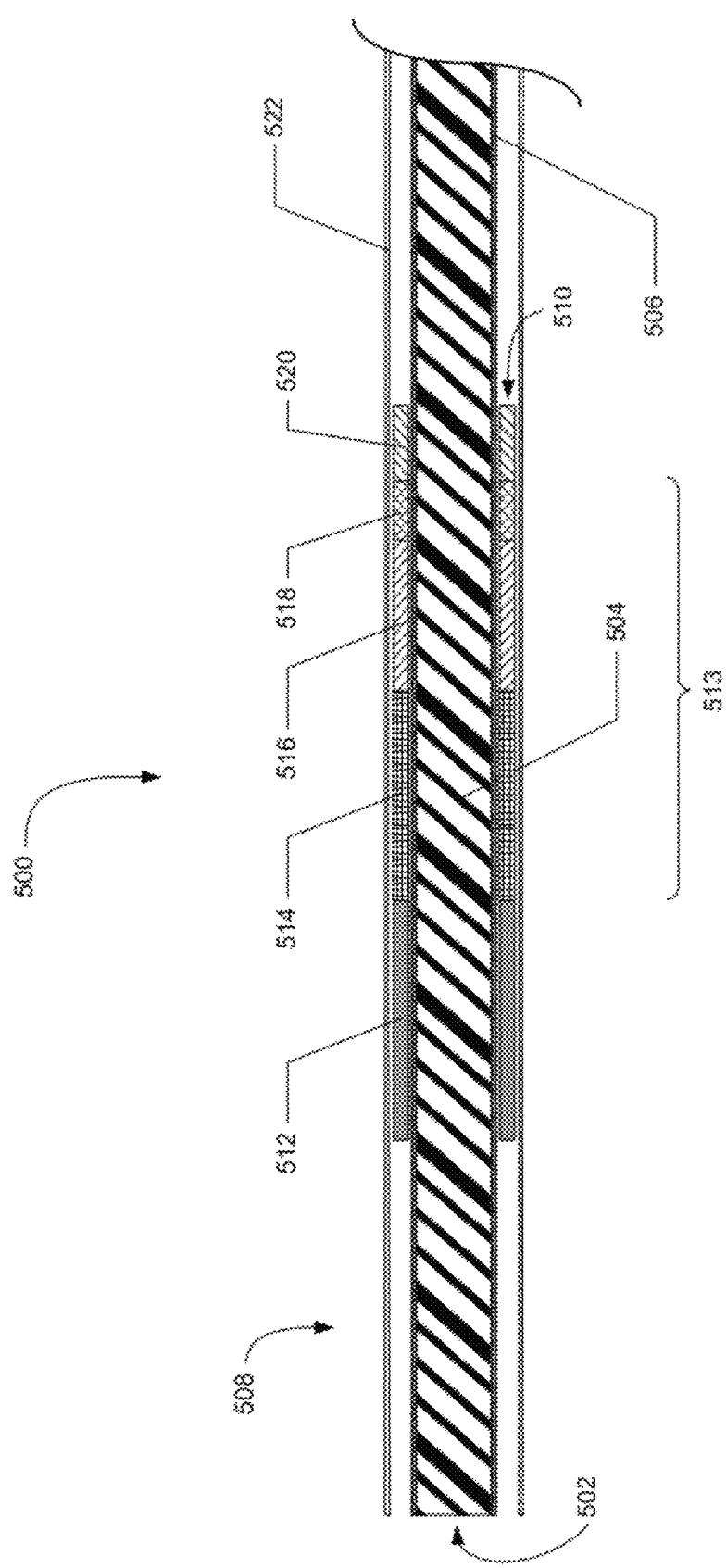
FIG. 6 is a partial sectional side view of one embodiment of an imaging window assembly fixture.

A flow diagram illustrating processing steps for manufacturing an imaging window embodying the invention is shown in FIG. 5. The corresponding imaging window assembly fixture 500 is shown in sectional side view in FIG. 6. An anti-stick coated mandrel 502 includes a mandrel 504 and a thin PTFE coating 506. The anti-stick coated mandrel 502 may have a diameter in the range 0.0225" to 0.0340", generally 0.0330", and may be used for loading of a tubing assembly 510. The tubing assembly 510 may include a midshaft tubing 512, an imaging window assembly 513, and a distal tubing 520 wherein the imaging window assembly 513 includes an imaging window proximal tubing 514, an imaging window middle tubing 516, and an imaging window distal tubing 518. The inner diameter of the midshaft tubing 512, imaging window proximal tubing 514, imaging window middle tubing 516, imaging window distal tubing 518, and soft tip tubing 520 may be constant in the range 0.024" to 0.038", generally 0.0335". The wall thickness of the imaging window proximal tubing 514, imaging window middle tubing 516, and imaging window distal tubing 518 may be in the range 0.001" to 0.007", generally 0.005". The midshaft tubing 512 may be composed of HDPE having a flexural modulus in the range 200 ksi to 250 ksi, generally 225 ksi. The imaging window assembly 513 decreases in stiffness progressing from proximal to distal direction.

The midshaft tubing 512 is trimmed in step 400 to a length in the range of 60 mm to 100 mm, generally 80 mm. The trimmed midshaft tubing 512 is loaded onto the PTFE-coated mandrel 502 in step 402. The proximal end of the midshaft tubing 512 may be positioned in the range 100 mm to 150 mm, generally 125 mm, from an end of the PTFE-coated mandrel 502. The distance from the end of the PTFE-coated mandrel 502 to the proximal end of the midshaft tubing 512 is referred to as the top clamping region 508. The length of the top clamping region 508 is sufficiently long to insure that the vertical laminator clamp does not clamp the midshaft tubing 512.

The imaging window proximal tubing 514 is then trimmed in step 404 to a length in the range of 40 mm to 100 mm, generally 70 mm. The trimmed imaging window proximal tubing 514 is loaded onto the PTFE-coated mandrel 502 in step 406 and positioned next to the midshaft tubing 512. The imaging window proximal tubing 514 may be composed of HDPE having a flexural modulus in the range 195 ksi to 245 ksi, generally 220 ksi.

The imaging window middle tubing 516 is then trimmed in step 408 to a length in the range of 40 mm to 100 mm, generally 50 mm. The trimmed imaging window middle tubing 516 is loaded onto the PTFE-coated mandrel 502 in step 410 and positioned next to the imaging window proximal tubing 514. The imaging window middle tubing 516 may be composed of MDPE having a flexural modulus in the range 155 ksi to 205 ksi, generally 180 ksi.

The imaging window distal tubing 518 is next trimmed in step 412 to a length in the range of 10 mm to 50 mm, generally 20 mm. The trimmed imaging window distal tubing 518 is loaded onto the PTFE-coated mandrel 502 in step 414 and positioned next to the imaging window middle tubing 516. The imaging window distal tubing 518 may be composed of LDPE having a flexural modulus in the range 35 ksi to 85 ksi, generally 60 ksi.

The distal tubing 520 is next trimmed in step 416 to a length in the range of 10 mm to 30 mm, generally 25 mm. The distal tubing 520 may also be composed of PE. The trimmed distal tubing 520 is loaded onto the PTFE-coated mandrel 502 in step 418 and positioned next to the imaging window distal tubing 518. The primary purpose of the distal tubing 520 is as a processing aid to prevent shifting the tubing assembly 510 position.

The tubing assembly 510 includes the sequence of midshaft tubing 512, imaging window proximal tubing 514, imaging window middle tubing 516, imaging window distal tubing 518, and distal tubing 520. Heat shrink tubing 522 is next loaded over the tubing assembly 510 and the top clamping region 508 of the PTFE-coated mandrel 502 in step 420. The heat shrink tubing 522 may be composed of fluorinated ethylene propylene (FEP). The heat shrink tubing 522 may have an inner diameter in the range 0.042" to 0.048", generally 0.045". The length of the heat shrink tubing 522 is sufficiently long to cover the length of the top clamping region 508 and the tubing assembly 510 and is at least 380 mm. Any gaps between the tubing assembly 510 sections are closed in step 422 by pushing the tubing assembly sections together. This insures that the tubing assembly 510 sections flow together when heated.

The imaging window assembly fixture 500 includes the PTFE-coated mandrel 502, the tubing window assembly 510, and the heat shrink tubing 522. The imaging window assembly fixture 500 is loaded into the vertical laminator in step 424 wherein the top clamping region 508 is fixed in position by means of a vertical laminator clamp.

The tubing sections of the tubing window assembly 510 are bonded in step 426 by means of a vertical laminator heater set to a temperature in the range of 500° F. to 700° F., generally 645° F. The vertical laminator heater is set sufficiently high to raise the temperature of the imaging window assembly fixture such that the tubing window assembly flows, but the heat shrink tubing does not flow. The transverse speed of a vertical laminator thermal nozzle affects the temperature of the imaging window assembly fixture and is in the range of 1 mm/s to 10 mm/s, generally 5 mm/s.

Following the bonding of the tubing sections, the imaging window assembly fixture 500 is removed from the vertical laminator in step 428. The heat shrink tubing 522 is removed from the imaging window assembly 500 in step 430 by means of a razor or other cutting tool taking particular care to not cut or abrade the tubing assembly 510. The tubing assembly 510 is then removed from the PTFE-coated mandrel 502 in step 432 wherein the tubing assembly includes the midshaft section 512, the imaging window assembly 513, and the soft tip 520.

Figure 7:
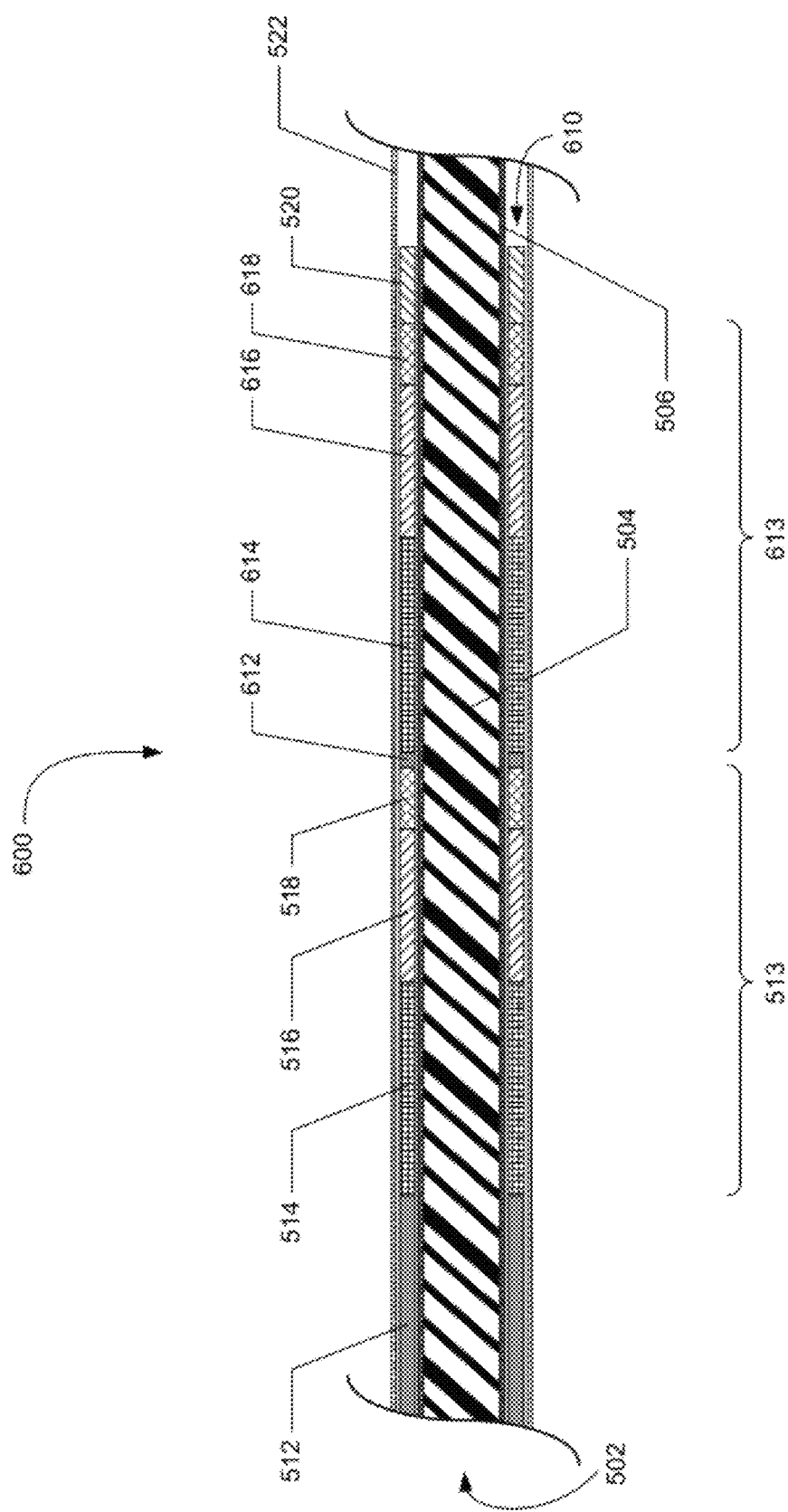
FIG. 7 is a partial sectional side view of another embodiment of an imaging window assembly fixture.

Referring now to FIG. 7, another embodiment of an imaging window assembly fixture 600 is shown wherein a tubing assembly 610 includes a first imaging window assembly 513 and a second imaging window assembly 613. A "divider" tubing 612 is loaded between the first imaging window assembly 513 and second imaging window assembly 613 wherein the divider tubing 612 may be composed of PE, the same material as the midshaft tubing 512. The primary purpose of the divider tubing 612 is as a processing aid to facilitate segmentation of the first imaging window assembly 513 and second imaging window assembly 613. The first imaging window assembly 513 includes a first imaging window proximal tubing 514, a first imaging window middle tubing 516, and a first imaging window distal tubing 518. The second imaging window assembly 613 includes a second imaging window proximal tubing 614, a second imaging window middle tubing 616, and a second imaging window distal tubing 618. An advantage of the alternative embodiment of an imaging window assembly fixture 600 is more than one imaging window assembly being manufactured on a PTFE-coated mandrel 502. After processing the imaging window assembly fixture 600 in a vertical laminator and removing the heat shrink tubing 522, the imaging window assemblies 513, 613 can be separated by making a roll-cut through the divider tubing 612 by means of a razor or other cutting tool. The tubing assembly 610 is then removed from the PTFE-coated mandrel 502.

Another embodiment of the tubing assembly may include three or more imaging window assemblies wherein the imaging window assemblies are separated by divider tubings. Further, additional imaging window assembly fixtures can be loaded into a vertical laminator wherein one imaging window assembly fixture is loaded for each vertical laminator station. In still another embodiment of the invention four imaging window assembly fixtures may be assembled, wherein each imaging window assembly fixture includes a tubing assembly having five imaging window assemblies separated by four divider tubings. A vertical laminator having at least four heating stations may be used to heat bond the tubing assemblies.

While particular embodiments of the present invention have been shown and described, modifications may be made, and it is therefore intended to cover in the appended claims all such changes and modifications which fall within the true spirit and scope of the invention.

What is claimed is:

1. In an imaging catheter, an imaging window, comprising:
    a first imaging window section, the first imaging window section having a proximal end, a distal end, and a finite length, a constant outer diameter and a constant inner diameter, and a first material having a flexural modulus; and
    a second imaging window section, the second imaging window section having a proximal end, a distal end, and a finite length, a constant outer diameter and a constant inner diameter, and a second material having a flexural modulus,
    wherein the flexural modulus of the first material is different than the flexural modulus of the second material, the catheter has a proximal end and a distal end, the first imaging window section is proximal to the second imaging window section, the distal end of the first imaging window section is bonded to the proximal end of the second imaging window section such that the first material at the distal end of the first imaging window section contacts the second material at the proximal end of the second imaging window section, the flexural modulus of the first material is greater than the flexural modulus of the second material, the constant outer diameter of the first imaging window section is equal to the constant outer diameter of the second imaging window section, the constant inner diameter of the first imaging window section is equal to the constant inner diameter of the second imaging window section, and the first and second materials are transparent to ultrasound energy.

2. The catheter of claim 1, wherein the first and second materials include polyethylene materials.

3. The catheter of claim 1, wherein the first and second materials each have imaging performance characteristics, and wherein the imaging performance characteristics of the first and second materials are equivalent.

4. In an imaging catheter, an imaging window, comprising:
    a plurality of serially aligned imaging window sections including a first imaging window section having a proximal end and a distal end, and a second imaging window section having a proximal end and a distal end, each imaging window section having a finite length and a constant outer diameter and a constant inner diameter and a material having a flexural modulus,
    wherein the flexural modulus of the material of each imaging window section is different from the flexural modulus of the material of each of the other imaging window sections, the distal end of the first imaging window section is bonded to the proximal end of the second imaging window section such that the material at the distal end of the first imaging window section contacts the material at the proximal end of the second imaging window section, the catheter has a proximal end and a distal end, the flexural modulus of the materials of the imaging window sections decreases from proximal sections to distal sections of the catheter, the constant outer diameter of each imaging window section being equal, the constant inner diameter of each imaging window section being equal, and each of the imaging window sections is transparent to ultrasound energy.

5. The catheter of claim 4, wherein each of the imaging window sections includes a polyethylene material.

6. The catheter of claim 4, wherein each of the imaging window sections has imaging performance characteristics and wherein the imaging performance characteristics of the imaging window sections are equivalent.

7. The catheter of claim 1, wherein the distal end of the first imaging window section flows together with the proximal end of the second imaging window section to preclude any gaps therebetween that are not transparent to ultrasound energy.

8. The catheter of claim 4, wherein the distal end of the first imaging window section flows together with the proximal end of the second imaging window section to preclude any gaps therebetween that are not transparent to ultrasound energy.

* * * * *